(12) United States Patent
Chin

(10) Patent No.: US 6,607,547 B1
(45) Date of Patent: Aug. 19, 2003

(54) LONGITUDINAL DILATOR AND METHOD

(75) Inventor: Albert K. Chin, Palo Alto, CA (US)

(73) Assignee: Origin Medsystems, Inc., Menlo Park, CA (US)

( * ) Notice: Subject to any disclaimer, the term of this patent is extended or adjusted under 35 U.S.C. 154(b) by 0 days.

(21) Appl. No.: 09/645,473

(22) Filed: Aug. 24, 2000

Related U.S. Application Data

(60) Provisional application No. 60/150,737, filed on Aug. 25, 1999.

(51) Int. Cl.$^7$ ............................................... A61B 17/00
(52) U.S. Cl. ........................................ 606/198; 606/190
(58) Field of Search ................................ 606/198, 192, 606/190, 159–191, 185, 194, 108; 604/104, 105; 600/201, 203, 204–208

(56) References Cited

U.S. PATENT DOCUMENTS

| | | | |
|---|---|---|---|
| 702,789 A | * | 6/1902 | Gibson ........................ 606/198 |
| 5,033,477 A | | 7/1991 | Chin et al. |
| 5,071,428 A | | 12/1991 | Chin et al. |
| 5,256,132 A | | 10/1993 | Snyders |
| 5,385,156 A | | 1/1995 | Oliva |
| 5,972,010 A | * | 10/1999 | Taheri ........................ 606/198 |
| 6,030,406 A | * | 2/2000 | Davis et al. ................. 606/190 |
| 6,077,218 A | | 6/2000 | Alferness |
| 6,237,605 B1 | | 5/2001 | Vaska et al. |
| 6,346,074 B1 | | 2/2002 | Roth |
| 6,478,028 B1 | | 11/2002 | Paolitto et al. |

\* cited by examiner

*Primary Examiner*—Kevin Truong
(74) *Attorney, Agent, or Firm*—Fenwick & West LLP

(57) ABSTRACT

Apparatus and method for dilation of tissue utilize a tissue expansion device positioned on an inner cannula with an outer overlying expansive sheath that expands upon translation of the tissue expansion device therethrough. The tissue expansion device may be an olive or wedge formed near the tip of the cannula, and the expansible sheath includes two elongated shells that are fixably attached near proximal ends, and that are resiliently connected near distal ends. Translating the tissue expansion device through the expansible sheath expands the dimension of the shells to provide even dilation of surrounding tissue. Additionally, tissue dilation is performed in one continuous motion of retracting the inner cannula through the expansible sheath or pushing the tissue expansion device through the expansible sheath. The outer expansible sheath may be removed from the inner cannula to provide a dissection instrument having minimal outer diameter. The tissue expansion device may provide two stage expansion from a minimal outer dimension in one configuration to a second larger outer dimension in response to an applied axial force to provide enhanced tissue dilation.

8 Claims, 7 Drawing Sheets

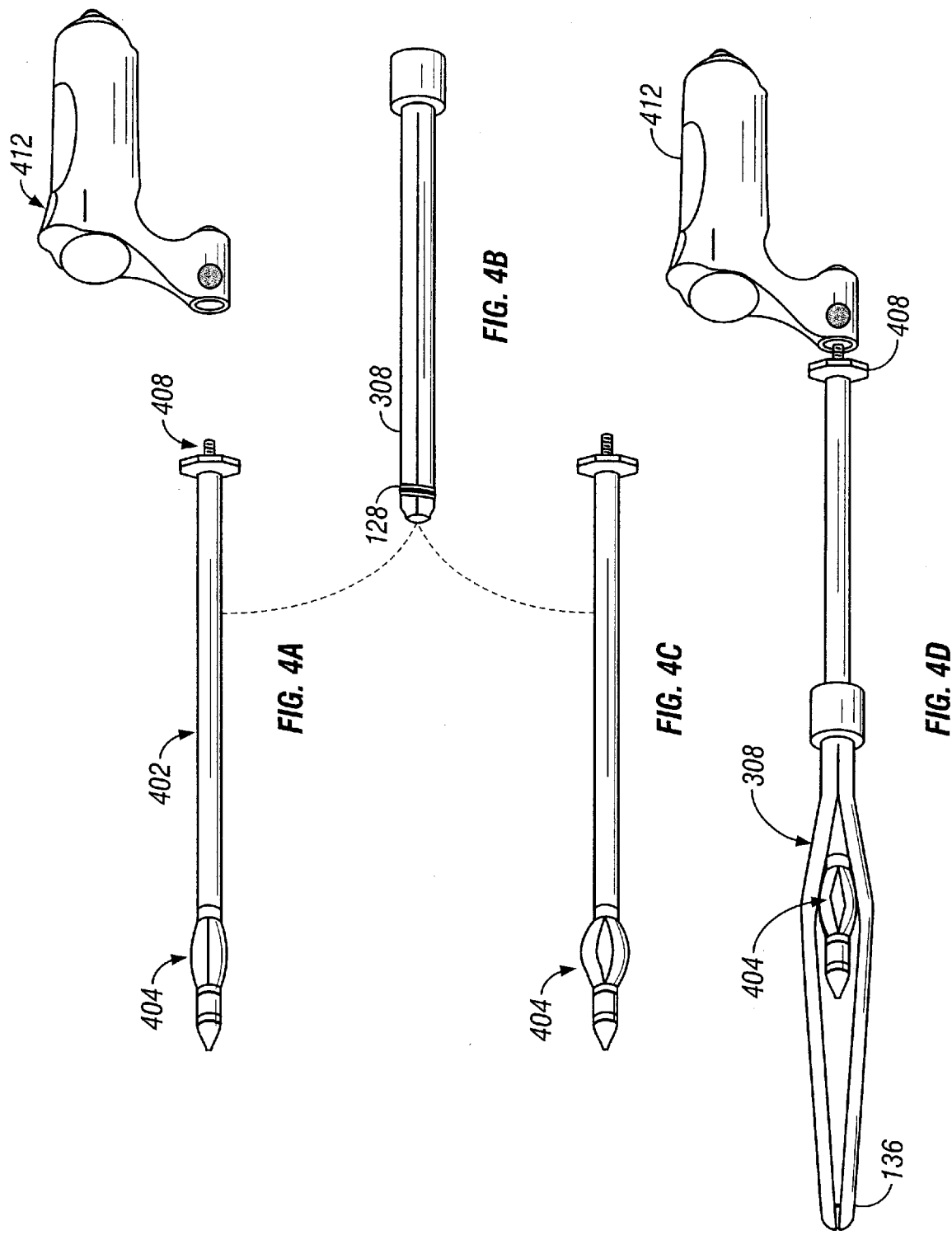

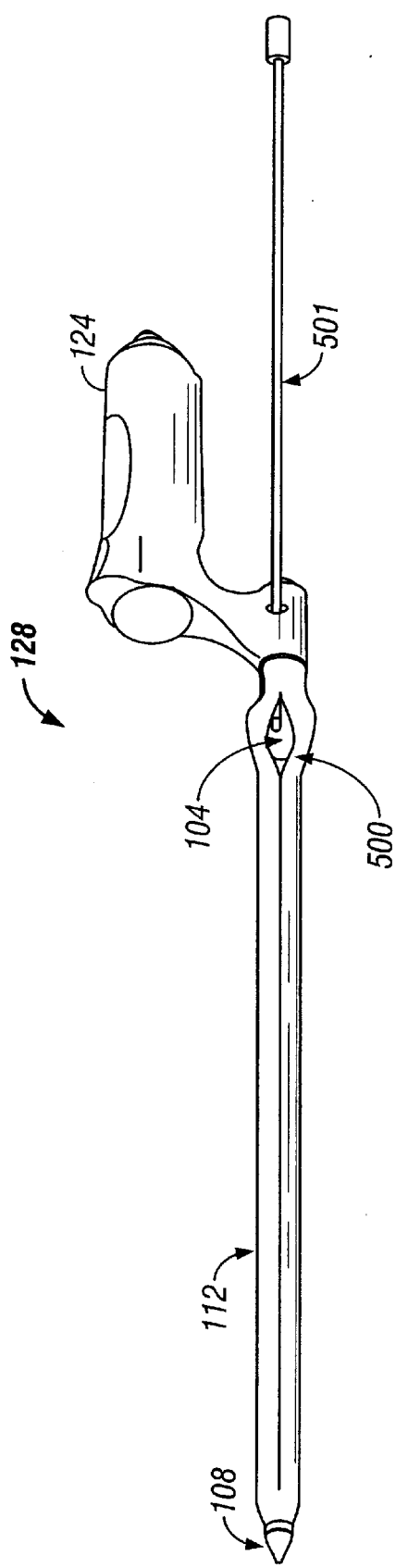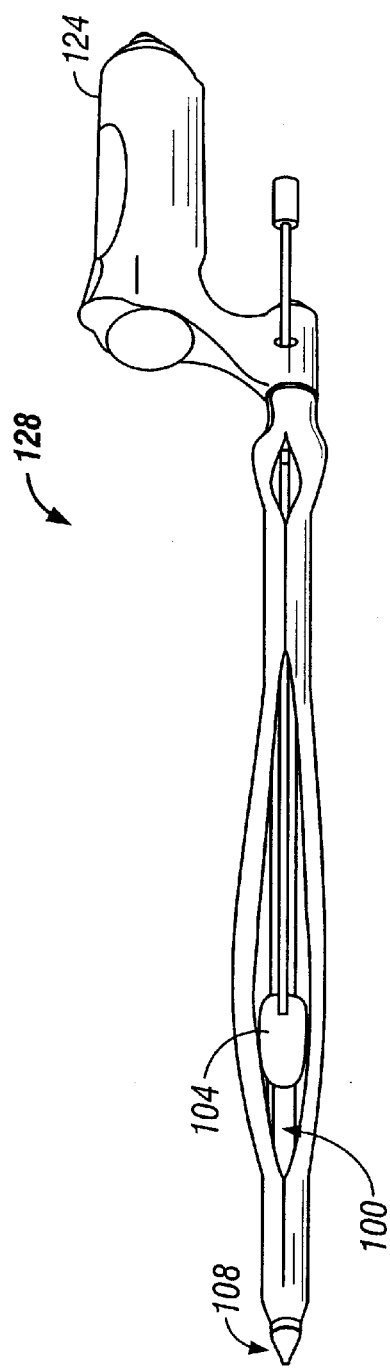
FIG. 5A
FIG. 5B

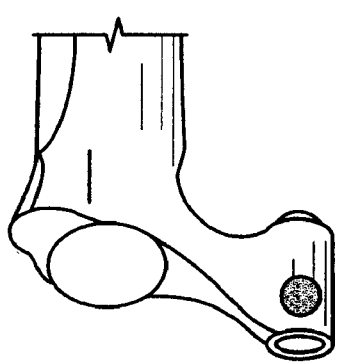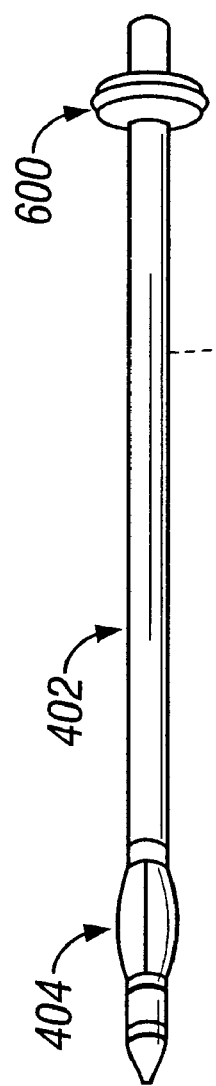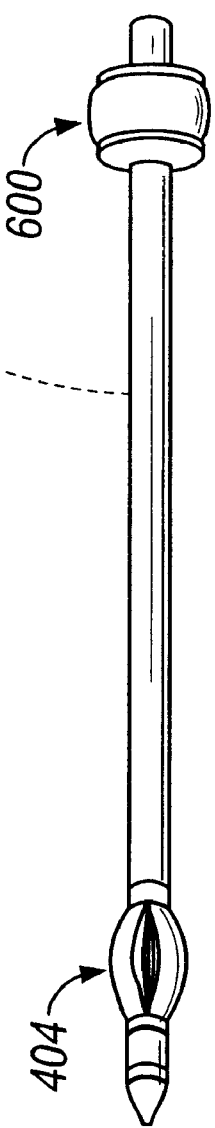
FIG. 6A
FIG. 6B
FIG. 6C

LONGITUDINAL DILATOR AND METHOD

RELATED APPLICATIONS

The present application claims priority from U.S. Provisional Patent Application No. 60/150,737, entitled "Longitudinal Mechanical Dilator", filed on Aug. 25, 1999, and U.S. Patent Application "Apparatus for Endoscopic Pericardial Access", filed on Aug. 9, 2000, which are both hereby incorporated by reference.

FIELD OF THE INVENTION

The present invention relates to the field of surgical apparatus, and, more particularly, to tissue dilation.

BACKGROUND OF THE INVENTION

Dilation of tissue is important for many surgical procedures, including vessel harvesting. Tissue must be dilated to allow atraumatic advancement of surgical instruments within the body to a surgical site. For example, to perform a vessel harvesting procedure, a ligation tool, typically maintained within a cannula providing endoscopic visualization, must be advanced to a vessel of interest to ligate the ends of the vessel and any intermediate side branches. However, prior to advancing the ligation tool, the path to the vessel end must be created while creating as little trauma to the surrounding tissue as possible. Many of the present systems used in endoscopic vessel harvesting incorporate a transparent tapered tip to dissect the vein from surrounding connective tissue, and then dilate the perivascular cavity by serially inflating a short balloon along the length of the cavity. Mechanical means of dilating the cavity have also been described, for example, such as those described in U.S. Pat. No. 6,030,406, including moving arms or cams which expand outward upon activation of a sleeve or a trigger. In these embodiments, a balloon or active mechanical dilator of short length is used, because the short length ensures that the dilators will be able to generate an adequate amount of force to successfully dilate the tunnel. For example, it is known that a short angioplasty balloon generates greater dilating force than a long angioplasty balloon. The wall tension of an inflated balloon is responsible for generating the dilating force. The longitudinal wall of a long balloon maintains less tension in the middle area of the balloon. This area of less tension corresponds to a diminished dilating force. Thus, many surgeons prefer using short balloons because a short balloon can maintain tension across the entire body. However, a short balloon or mechanical dilator in a tissue-dilating system must be activated multiple times along the length of the tunnel to achieve a complete expansion of the tunnel. This repeated motion may tire the hand of a surgeon performing the procedure, and, further, stepwise dilation may result in formation of an uneven tunnel, with an irregular inner contour. Therefore, an apparatus and method are needed that provide adequate tissue-dilating force, result in an even dilation, and do not require multiple repeated movements to complete the dilation procedure.

SUMMARY OF INVENTION

Apparatus and method according to the present invention perform uniform dilation of tissue while avoiding repetitive actuations and high level forces applied by the user. In a preferred embodiment, a tissue expanding device is pulled longitudinally along an expansible sheath to dilate an extravascular tunnel. In one embodiment, the tissue expansion device is positioned immediately proximal to a transparent tapered tip of a cannula and is formed as a wedge or olive. The distal end of the expansible sheath is compressed against the outer surface of the cannula by a resilient connector, and, in one embodiment, the expansible sheath ends in a solid sleeve proximally. Then, as the tissue expansion device is retracted through the expansible sheath, the resilient connector expands outwardly to permit the tissue expansion device to be retracted into the expansible sheath. As the tissue expansion device is moved toward the proximal end of the cannula through the expansible sheath, the sheath expands concurrently with it, providing an even dilation of the surrounding tissue. The tissue dilation may be obtained through one smooth motion of pulling back on the inner cannula, thus avoiding repetitive motions. The sheath is preferably made of a rigid or semi-rigid material and the tissue expansion device has an enlarged maximal dimension. The force exerted on surrounding tissue by the expansion of the sheath as a result of the movement of the tissue expansion device within the sheath is therefore sufficiently high to provide adequate dilation of the surrounding tissue.

An alternate tissue expansion device may incorporate an expansible sheath that ends in a solid transparent tapered cone distally and a solid sleeve proximally. Adjacent to the proximal solid sleeve is a sheath of an enlarged diameter that houses a wedge or olive that slides along the cannula to expand the expansible sleeve. In this embodiment, the tissue expansion device is pushed along the cannula within the expansible sheath using a push rod that extends in a proximal direction from its attachment point to the olive. As the tissue expansion device is pushed through the sheath, the sheath expands and dilates the surrounding tissue.

A method for performing a vessel harvesting operation in accordance with the present invention includes incising the skin overlying a vessel of interest, bluntly dissecting the tissue overlying the vessel, advancing the cannula to the end of the vessel under endoscopic visualization, retracting the tissue expansion device longitudinally toward the proximal end of the device or pushing the tissue expansion device toward the distal end of the device, and thus concurrently dilating the tissue around the vessel, extending the tissue expansion device to its original distal position to contract the sheath for additional dilation, and then removing the cannula from the body. Thereafter, additional instruments may be inserted into the dilated tunnel to perform the required surgical operations.

BRIEF DESCRIPTION OF THE DRAWINGS

FIGS. 4A–4D are perspective views of a split tissue expansion device embodiment in accordance with the present invention.

FIGS. 5A–B are perspective views of an alternate embodiment of the longitudinal mechanical dilator of the present invention.

FIGS. 6A–G are perspective views of alternate embodiments of axial compressor mechanisms in accordance with the present invention.

DETAILED DESCRIPTION OF THE PREFERRED EMBODIMENTS

Figure 1:
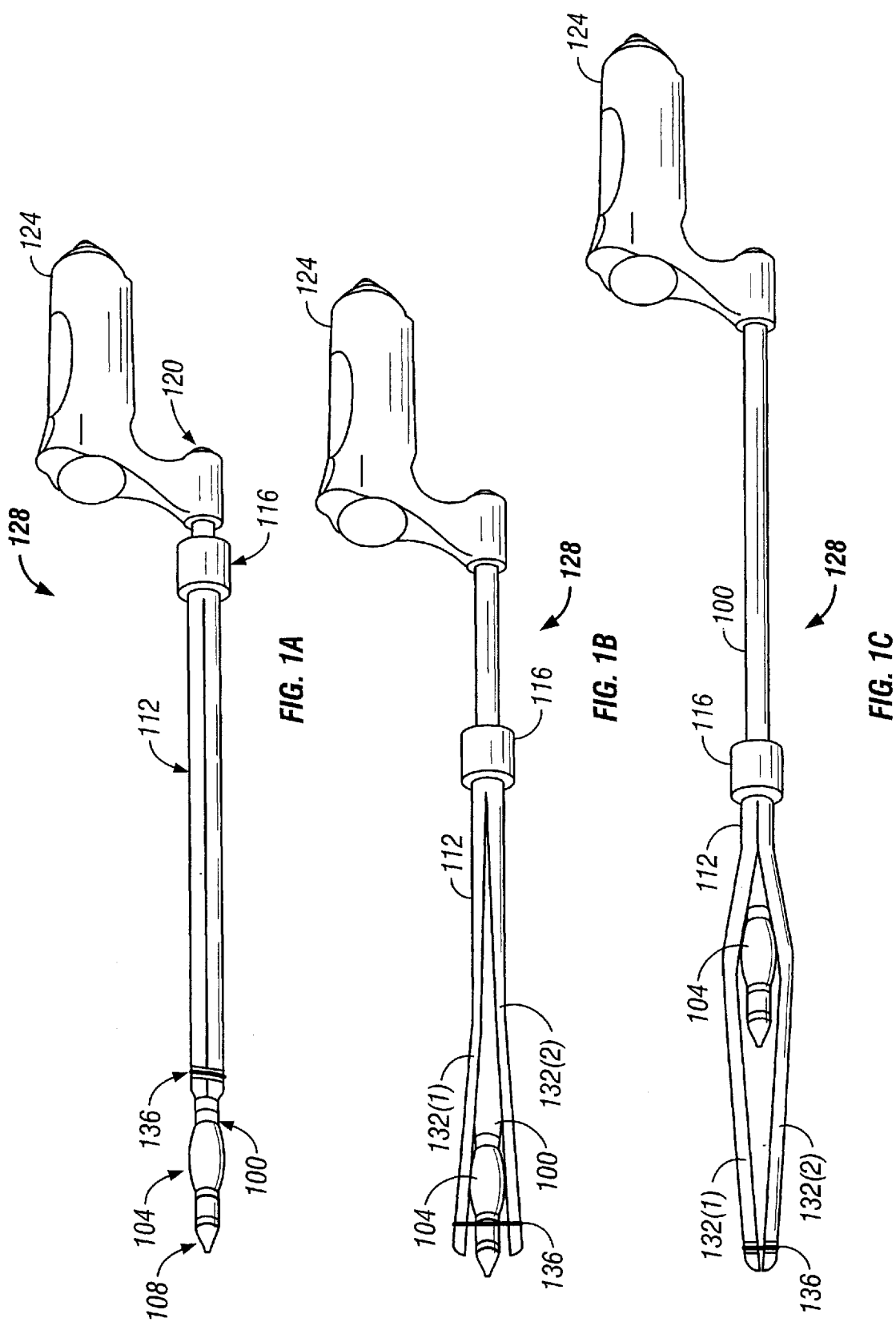
FIG. 1A is a perspective view of a longitudinal mechanical dilator in accordance with the present invention.
FIG. 1B is a perspective view of the dilator of FIG. 1A in which the inner cannula is partially withdrawn through an expansible sheath in accordance with the present invention.
FIG. 1C is a perspective view of the dilator of FIG. 1B in which the inner cannula is further withdrawn through the expansive sheath in accordance with the present invention.

FIG. 1A is a perspective view of a longitudinal mechanical dilator 128 in accordance with the present invention. The dilator 128 preferably comprises an inner cannula 100 and an outer expansible sheath 112. A tissue expansion device 104 is disposed on the distal end of the inner cannula 100. In one embodiment, the outer expansible sheath 112 is preferably split longitudinally into two shells 132. Alternatively, the outer expansible sheath 112 is comprised of a flexible material that expands upon moving the tissue expansion device 104 within the sheath 112. In one embodiment, the distal end of the outer expansible sheath 112 is compressed against the outer surface of the inner cannula 100 by a resilient connector 136. The proximal end of the outer expansible sheath 112 preferably includes an integrated segment, for example, within a handle 116. Thus, upon retracting the tissue expansion device 104 through the distal end of the outer expansible sheath 112, as shown in FIG. 1B, the tissue expansion device 104 exerts an outward force against the outer expansible sheath 112 which facilitates expansion of the resilient connector 136. As shown in FIG. 1C, in this embodiment, the tissue expansion device 104 is then retracted toward the proximal end of the expansible sheath 112, pushing the shells 132 outward and thus dilating any surrounding tissue. Further movement of the tissue expansion device 104 in the proximal direction is restrained upon reaching the integrated end of the expansible sheath 112. In an alternate embodiment, as shown in FIG. 5A, the tissue expansion device 104 may be housed in an enlarged portion 500 of the outer expansible sheath 112 and is slidably attached to the inner cannula 100+. A push rod 501 attached to the tissue expansion device 104 is used to translate the tissue expansion device 104 along the inner cannula 100, exerting an outward force against the outer expansible sheath 112 as the expansion device 104 is moved distally and proximally. As shown in FIG. 5B, as the tissue expansion device is moved within the expansible sheath 112 along the axis of the inner cannula 100, the expansible sheath 112 expands responsively.

In a preferred embodiment, the longitudinal mechanical dilator 128 is used for vessel harvesting procedures under endoscopic visualization. In this embodiment, the inner cannula 100 has an endoscopic lumen 120 for housing an endoscope and has a transparent tip 108 for viewing therethrough. In a preferred embodiment, the transparent tip 108 is tapered to provide improved visualization and dissection capabilities. The tissue expansion device 104 may be formed as a wedge or in an olive shape. The tissue expansion device 104 is preferably formed of Teflon or polyurethane, or polycarbonate, or the like, to form a rigid shape which compresses or otherwise displaces tissue on the walls of the surgical cavity to form an enlarged surgical cavity. In an alternate embodiment, the tissue expansion device 104 comprises resilient foam which compresses in response to an applied external force. One preferred wedge or olive is described in co-pending application "Tissue Dissection Apparatus and Method", Ser. No. 09/413,012, filed Oct. 10, 1999. The tissue expansion device 104 is preferably situated immediately proximal to the tip 108 of the dilator 128. The tissue expansion device 104 may be formed as an integral part of the tip 108, or may be formed independent of the tip 108 as part of the elongated body of the cannula 100. The cannula 100 is preferably substantially rigidly formed to provide the support for the axial force exerted against the expansible sheath 112. The cannula 100 may be made from a variety or combination of bioinert, substantially inelastic materials, such as stainless steel, polyethylene, polyurethane, polyvinyl chloride, polyimide plastic, and the like. Handle 124 is ergonomically formed to allow a surgeon to easily and comfortably manipulate cannula 100 within a surgical cavity.

The expansible sheath 112 preferably includes a solid or rigid segment near the proximal end, as described above, although alternatively the sheath 112 may comprise two independent shells that are fixably attached at their proximal ends. The solid or rigid segment may be of an increased diameter to serve as a separate handle 116 for convenient gripping by a surgeon. For example, when the surgeon retracts the inner cannula 100, the surgeon may grip handle 116 to maintain the outer expansible sheath 112 at the location where dilation is desired. In one embodiment, the outer diameter of the tissue expansion device 104 combined with the outer diameter of the expansible sheath 112, and any added outer elastic covering (not shown, for clarity), are selected to permit the longitudinal mechanical dilator 128 to fit through a standard 12 mm diameter gas insufflation port, as vessel dissection is typically performed with concurrent gas insufflation. In this embodiment, as the tissue expansion device 104 is pushed or pulled along the inner cannula 100, the sheath 112 expands to approximately a 20 mm outer dimension. In embodiments in which gas insufflation is not used, or in embodiments in which the ports are of different sizes, the sizes of the components of the dilator 128 may be adjusted accordingly.

Figure 2:
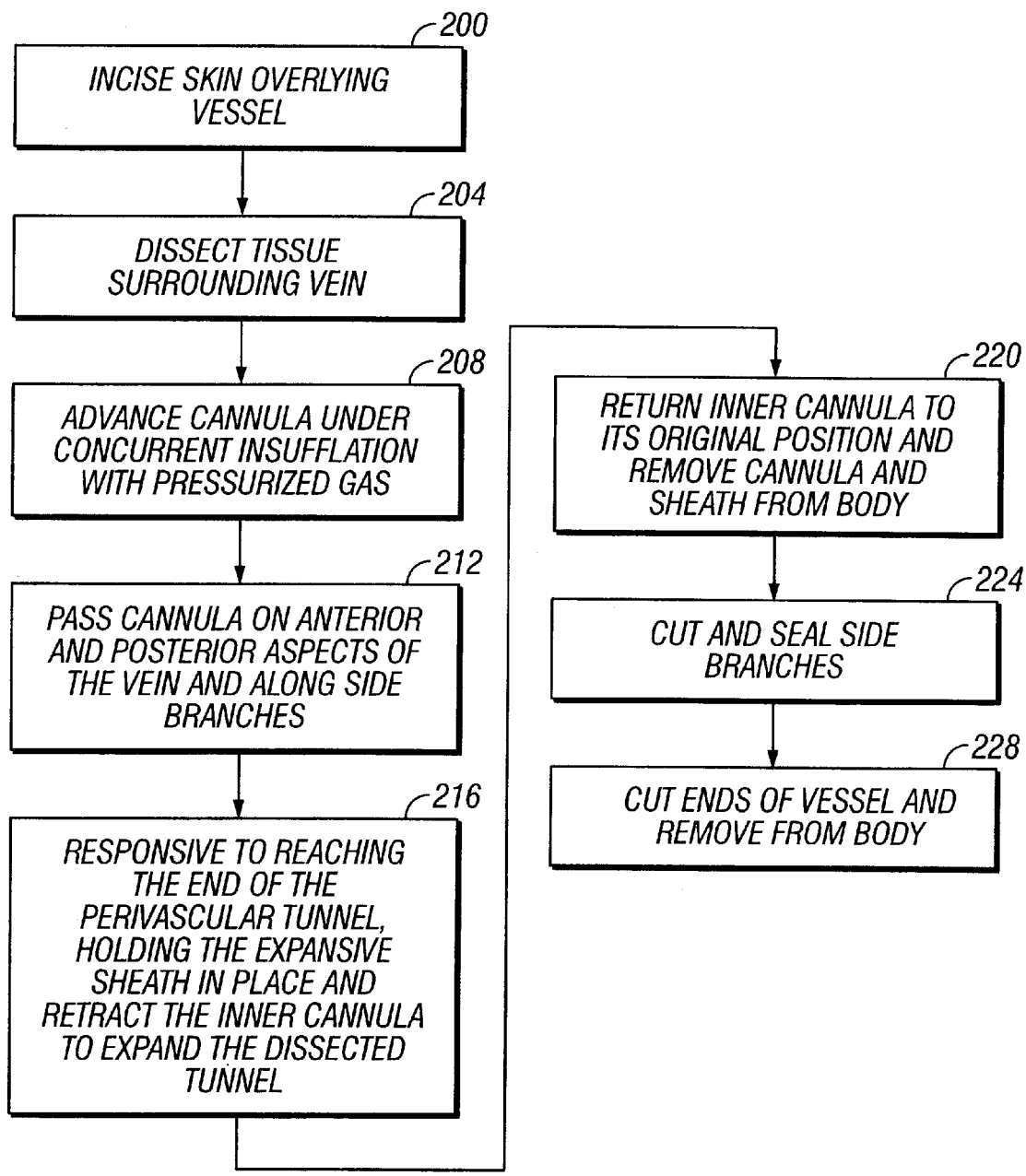
FIG. 2 is a flow chart illustrating a method of dilating tissue in accordance with the present invention.

FIG. 2 is a flow chart illustrating a method of dilating tissue in accordance with the present invention. Specifically, a method of harvesting a vein is illustrated. First, the surgeon makes a small incision 200 in the skin overlying the vessel of interest, for example, the saphenous vein. Then, the surgeon bluntly dissects 204 connective tissue covering the vein to expose the adventitial surface of the vein. The surgeon advances 208 a cannula with a transparent tapered tip in contact with the adventitial surface of the vein under endoscopic visualization through the transparent tip, and, optionally, under concurrent insufflation of the tunnel with pressurized gas to dissect an initial tunnel along the vein. At this stage in the procedure, the longitudinal mechanical dilator 128, a conventional endoscopic cannula with a transparent tapered tip, or any other method of initially dissecting a tunnel may be used in accordance with the present invention. The insufflation of the tunnel provides additional dilation and helps maintain the shape of the tunnel when the device is withdrawn. Then, the surgeon passes 212 the tip of the cannula along the anterior and posterior aspects of the vein and around the side branches to dissect a tunnel along the selected length of the vein. If a device other than the longitudinal mechanical dilator 128 of the present invention is being used, such other device is withdrawn and the longitudinal mechanical dilator 128 is inserted into the incision. If the longitudinal mechanical dilator 128 is being used to dissect the initial tunnel, then it is advanced to the end of the perivascular tunnel under endoscopic vision through the transparent tip 108, and, holding the handle 116 of the expansible sheath 112 stationary, the surgeon pulls or retracts 216 the tissue expansion device 104 on the inner cannula 100 through the expansible sheath 112 to expand the shells 132 and thereby further dilate tissue in the dissected tunnel and create a zone of expansion within the tunnel. Alternatively, the surgeon pushes the tissue expansion device 112 to the distal end of the dilator 128 to create a zone of expansion in the dissected tunnel. The zone of expansion corresponds to the region of the expansible sheath 112 under which the tissue expansion device lies. This zone extends from the distal to the proximal end of the tunnel as the tissue expansion device 104 is pulled backwards or pushed forwards. Thus, an evenly shaped zone of expansion is formed by the translation of the tissue expansion device 104 through the expansible sheath 112. Additionally, the dilation may be generated by one smooth motion of pulling back the inner cannula 100 or pushing the tissue expansion device 104, and thus the repetitive motions of conventional systems are avoided. Finally, the size of the tissue expansion device 104 and the rigidity of the shells 132 create a sufficiently large tunnel within which additional instruments can be maneuvered.

After the tunnel is dilated, the surgeon returns 220 the tissue expansion device 104 to its original position to contract the expansible sheath 112, and the dilator 128 is removed from the body. Contracting the expansible sheath 112 prior to removal minimizes the trauma to surrounding tissue caused by the longitudinal mechanical dilator 128. Then, the surgeon inserts additional instruments within the dilated tunnel to seal or apply clips and cut 224 the side branches of the vessel to be harvested. Finally, the surgeon cuts the two ends of the vessel and removes 228 the vessel from the body.

Figure 3:
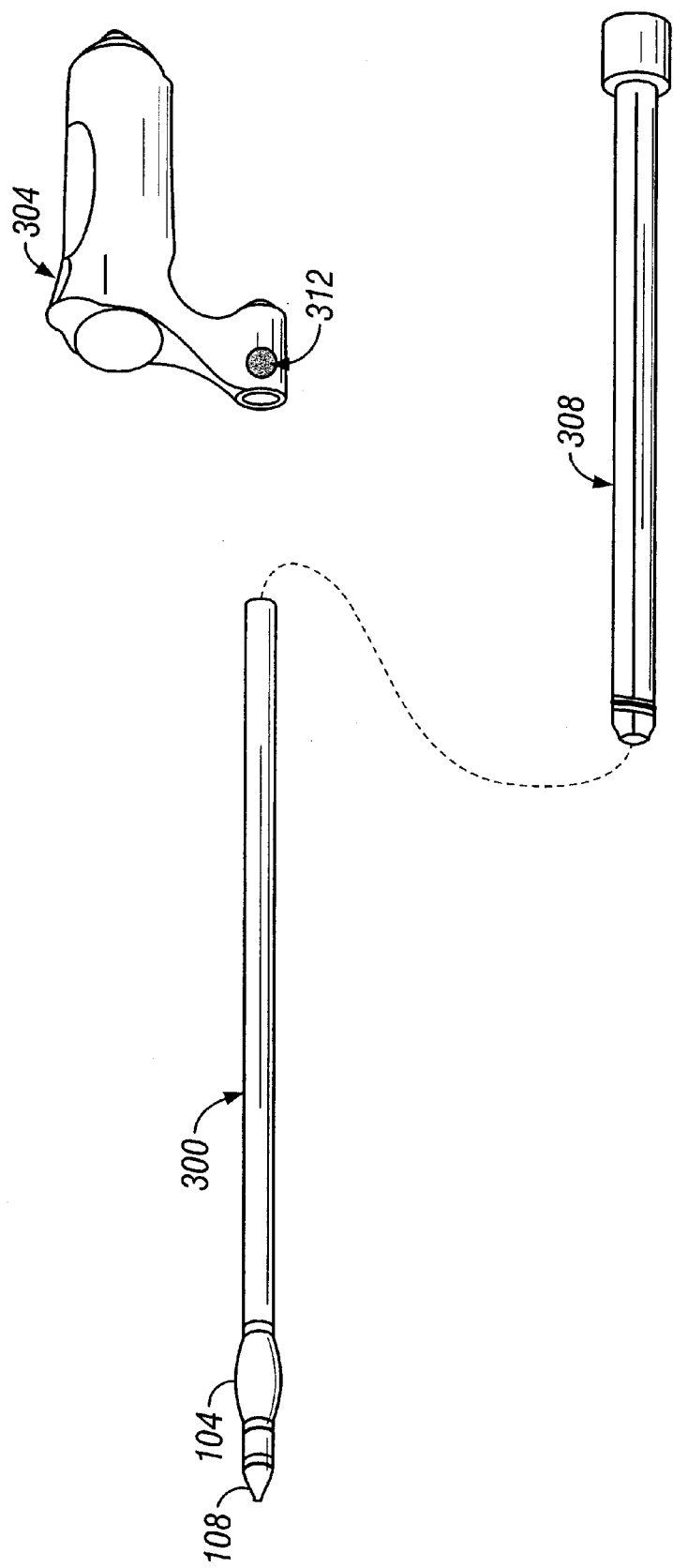
FIG. 3 is a perspective exploded view illustrating an alternate embodiment of the longitudinal mechanical dilator in which the expansible sheath is removable from the inner cannula.

FIG. 3 is a perspective, exploded view illustrating an alternate embodiment of a longitudinal mechanical dilator in which an expansible sheath is removable from an inner cannula. In this embodiment, the inner cannula 300 detaches from the handle 304 to allow the expansible sheath 308 to be removed from and added to the inner cannula 300 and handle 304 when desired. This embodiment provides a dissection cannula 300 of a smaller outer diameter along the majority of its length with the exception of the region of the tissue expansion device 104. Thus, this dissection device 300 may be used to provide initial dissection as described above in connection with FIG. 2, with increased tip maneuverability due to the small diameter of the cannula 300 for dissecting the vessel from the surrounding connective tissue. In one embodiment, the expansible sheath 308 is made removable by attaching a locking mechanism 312 to the handle 304. When the surgeon wants to remove the sheath 308, the surgeon can unlock the end of the inner cannula 300 from the handle 304 and remove the sheath 308 by sliding the sheath 308 in a proximal direction. To place the sheath 308 on the cannula 300, the surgeon unlocks and removes the handle 304, slides the sheath 308 onto the cannula 300, and then locks the handle 304 back in place. In one embodiment, the locking mechanism 312 is a threaded thumbscrew that fixes the proximal end of the inner cannula 300 in place upon being tightened against the inner cannula 300.

FIG. 4A illustrates another embodiment of the longitudinal mechanical dilator of the present invention that provides two-stage dilation. In one embodiment, a tissue expansion device 404 is split longitudinally into two or more sections as shown in FIG. 4A and an axial compressor mechanism 408, in one embodiment including a threaded shaft as later described herein, compresses the tissue expansion device 404 when dilation is sought to cause the split tissue expansion device 404 to expand. Thus, the split tissue expansion device 404 remains in a closed configuration having a minimal outer diameter when dilation is not required, and then can be expanded to a greater outer diameter when dilation is required. In one embodiment, the inner cannula 400 extends back to the handle 412, and a proximal portion of the inner cannula 400 is externally threaded. A sleeve 402 lies outside the inner cannula 400 and abuts tissue expansion device 404. In this embodiment, the axial compressor 408 is a threaded nut that is positioned on the proximal end of the inner cannula 400. When the threaded nut is rotated, the sleeve 402 compresses the tissue expansion device 404. Upon rotating the threaded nut, the distal end of the inner cannula 400 adjacent the proximal end of the split tissue dilation device 404 exerts an axially directed force against the split tissue dilation device. The distal end of the split tissue dilation device 404 is fixably attached to the inner cannula 400 and the proximal end is slidably attached. Therefore, as the distal end of the inner cannula 400 presses against the split tissue dilation device 404, the dilation device 404 is compressed and expands in diameter as shown in FIG. 4C. The expanded tissue expansion device 404 is retracted through the outer expansible sheath 308, as shown in FIG. 4D, to expand the outer dimension of the sheath 308 to a heightened dimension that may exceed 20 mm. Thus, this embodiment provides a cannula 400 that dissects an initial tunnel with heightened maneuverability and minimal applied force. However, by adding the outer expansible sheath 308 and compressing the tissue dilation device 404, the instrument 400 can be used to dilate a large tunnel within the tissue.

Figure 6D:
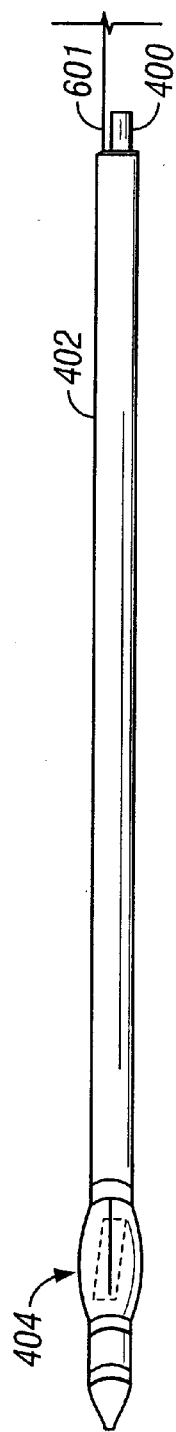
Figure 6E:
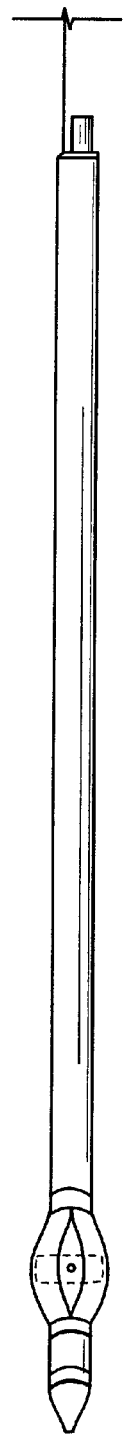
Figure 6F:
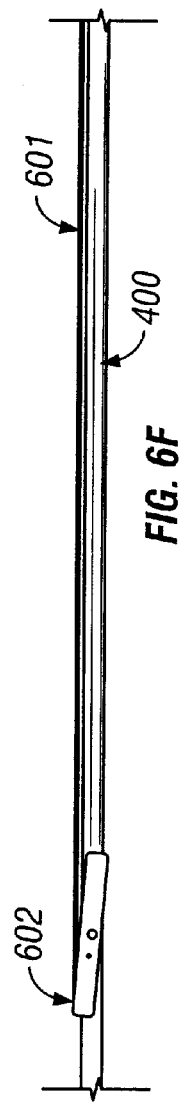
Figure 6G:
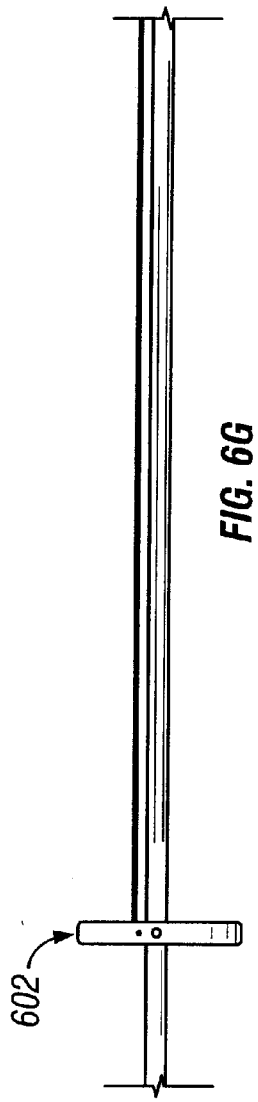

Other mechanisms for compressing the tissue dilation device 404 may also be used in accordance with the present invention. For example, as shown in FIGS. 6A–6C, an inflatable cuff 600 may substitute for the threaded nut used as axial compressor mechanism 408 in the embodiment of FIGS. 4A–C described above. Expansion of the inflatable cuff 600 using a syringe (not shown) moves the inner cannula 400 in an axial direction and consequently compresses the tissue dilation device 404, forcing it to expand. Alternatively, a mechanical mechanism may be used to as the axial compressor mechanism 408. For example, as shown in FIGS. 6D–6E, an actuation rod 601 may rotate a lever 602 hinged to the inner cannula 400. The lever 602 exerts force against the expansion device 404 to increase its outer diameter. FIGS. 6D and 6E show the split tissue expansion device 404 in its relaxed and expanded states respectively. FIGS. 6F and 6G show the lever mechanism 602 corresponding to the states shown in FIGS. 6D and 6E.

The present invention has been described above in relation to vessel harvesting. However, it should be noted that the apparatus and method of the present invention may also be utilized in procedures, for example, requiring access to the peritoneum, the dura mater, or any membrane overlying a sensitive organ, for example, the spine, the brain, or the stomach.

What is claimed is:
1. An apparatus for performing dilation of tissue comprising:
an inner cannula having a lumen therethough for receiving an endoscope therein to a distal end thereof, and having a transparent tip positioned at the distal end of the inner cannula to facilitate visualization through the tip;
an expansion device disposed near the distal end of the inner cannula having a maximal dimension greater than a maximal dimension of the inner cannula; and
an outer sheath expandable in an outward direction disposed over the inner cannula to expand outwardly in response to the expansion device of the inner cannula being disposed within the outer sheath.

2. The apparatus of claim 1 wherein the expansion device is formed in an olive configuration.

3. The apparatus of claim 1 wherein the expansion device is solid.

4. The apparatus of claim 1, wherein the outer sheath further comprises:

first and second elongated shells, and a resilient member disposed about the first and second shells to resiliently retain the first and second shells in contiguous relationship.

5. The apparatus of claim 4 wherein the resilient member is disposed about the first and second shells near distal ends thereof.

6. The apparatus of claim 4 wherein proximal ends of the first and second shells are retained in fixed positioned relationship.

7. The apparatus of claim 4 wherein distal ends of the first and second elongated shells are laterally separable and the resilient member resiliently retains the distal end of the first shell contiguous to the distal end of the second shell, for providing a first smaller dimension at a distal end of the outer sheath in the absence of a lateral expansion force applied between the first and second shells of the outer sheath, and for stabilizing the distal ends of the first and second shells during lateral separation thereof to a second larger dimension in response to a lateral expansion force applied between the first and second shells in response to the passing of the expansion device through a portion of the length of the first and second shells.

8. The apparatus of claim 1 wherein the first and second shells of the outer sheath are formed of flexible material to allow the shells to bend responsive to passing of the expansion device through the outer sheath.

* * * * *